Figure 1:
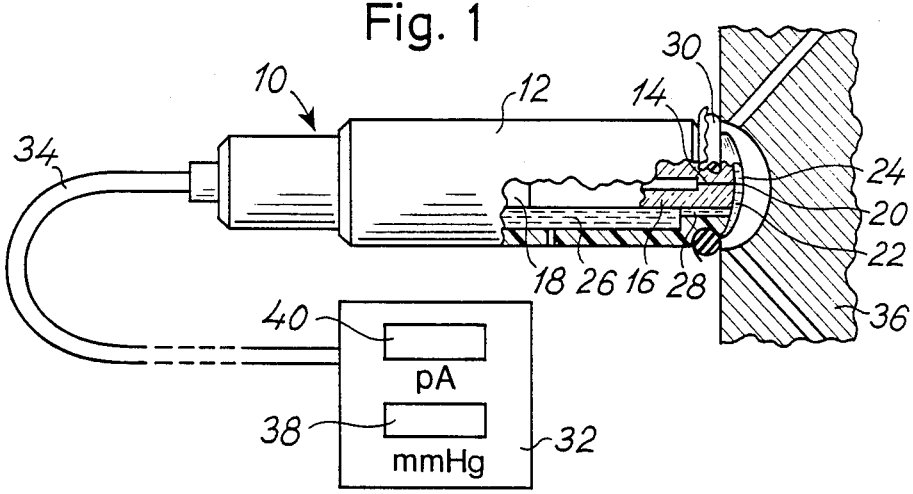

United States Patent [19]
Christiansen et al.

[11] Patent Number: 4,780,192
[45] Date of Patent: Oct. 25, 1988

[54] POLAROGRAPHIC MEASURING ELECTRODE DEVICE

[75] Inventors: Torben F. Christiansen, Holte; Finn Kokholm, Copenhagen, both of Denmark

[73] Assignee: Radiometer A/S, Copenhagen, Denmark

[21] Appl. No.: 106,959

[22] Filed: Oct. 14, 1987

Related U.S. Application Data

[63] Continuation of Ser. No. 875,645, Jun. 18, 1986, abandoned.

[30] Foreign Application Priority Data

Jun. 18, 1985 [DK] Denmark .............................. 2738/85

[51] Int. Cl.$^4$ ...................... G01N 27/30; G01N 27/54
[52] U.S. Cl. .................................................. 204/415
[58] Field of Search ............... 204/415, 1 P; 502/339; 128/635

[56] References Cited

U.S. PATENT DOCUMENTS 4,290,431 9/1981 Herbert et al. ...................... 128/635

FOREIGN PATENT DOCUMENTS 0056566 7/1982 European Pat. Off. .

OTHER PUBLICATIONS

Eric K. Rideal et al., "Catalysis in Theory and Practice", pp. 2, 389 & 390, (1919).
K. G. Schick et al., Anal Chem., vol. 48, No. 14, pp. 2186–2188, Dec. 1976.
Notice by Lloyd et al. in Proceedings of the Physiological Society, Dec. 1969, pp. 29–30.
Review of Physiological Chemistry, 16th. Ed., Lange Medical Publications, pp. 182 and 229.
Principles of Biochemistry, Ed. by A. L. Lehninger, Worth Publishers, Inc., 1982, p. 270.

Primary Examiner—G. L. Kaplan
Attorney, Agent, or Firm—Bryan, Cave, McPheeters & McRoberts

[57] ABSTRACT

An electrochemical measuring electrode device (10) for polarographically measuring the partial pressure of oxygen in an electrolytic medium comprises a cathode (14) which is capable of reducing oxygen and defines an exposed oxygen-reducing cathode surface (20), an anode (18), which defines an exposed anode surface which is arranged relative to the exposed oxygen-reducing cathode surface so as to communicate electrolytically therewith through the electrolytic medium, and a membrane (24), which covers the exposed oxygen-reducing cathode surface and further defines an electrolyte chamber (22) in which the electrolytic medium is confined. In order to effectively promote the decomposition of $H_2O_2$ generated in the electrolytic medium as an oxygen reduction intermediate and thereby reduce the response time of the electrode, a stable, non-biological catalytic means is provided catalytically communicating with the $H_2O_2$. The stable, non-biological catalytic means is preferably constituted by platinum black particles which may be received by the membrane at a central region (42) thereof or alternatively be received by a support structure which may further constitute a covering of at least part of the membrane (24).

The platinum black particles may be pressed into a foil material constituting a base material of the membrane or alternatively be applied in a suspension to the membrane whereupon the suspension is solidified.

9 Claims, 4 Drawing Sheets

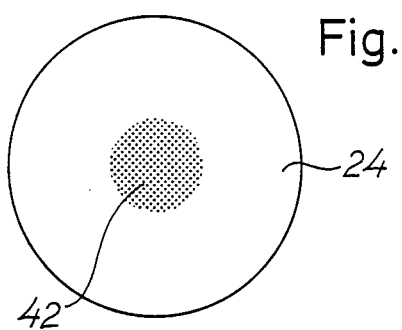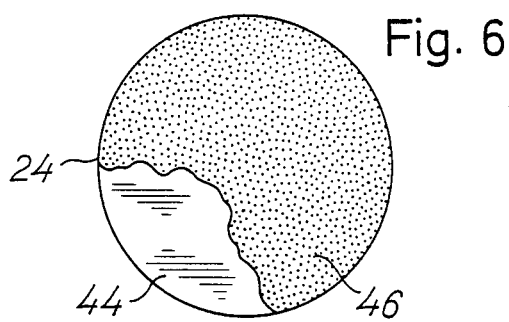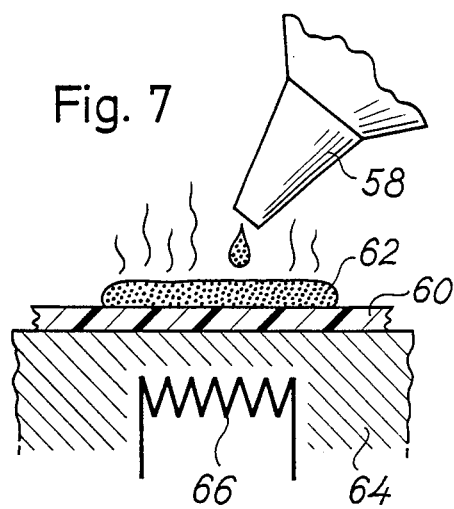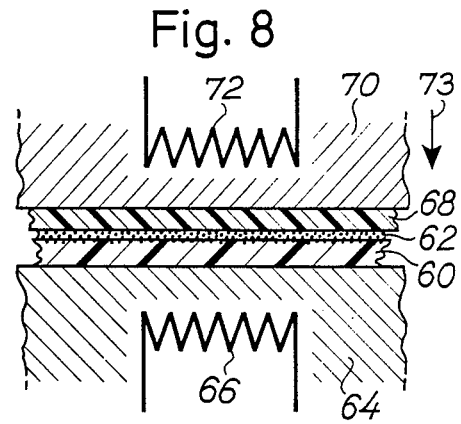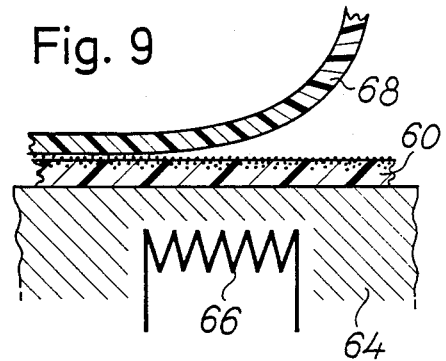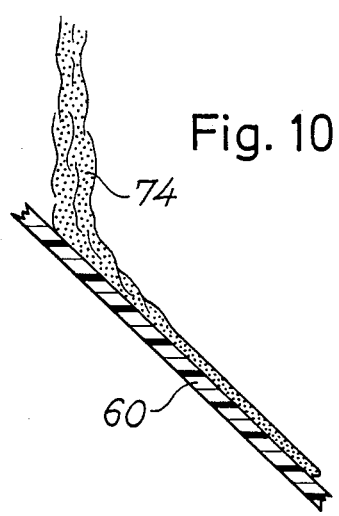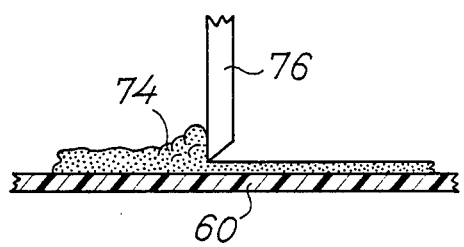

POLAROGRAPHIC MEASURING ELECTRODE DEVICE

This is a continuation of U.S. application Ser. No. 875,645, filed June 18, 1986, now abandoned.

An electrochemical measuring electrode device for polarographically measuring the partial pressure of oxygen, a membrane for an electrochemical measuring electrode devie and a method of preparing a membrane for an electrochemical measuring electrode device.

The present invention relates to an electrochemical measuring electrode device for polarographically measuring the partial pressure of oxygen. It is well-known to measure the partial pressure of oxygen by means of a polarographic measuring electrode device. A particularly relevant type of polarographic electrode device is the electrode device of the CLARK type. The expression "the electrochemical measuring electrode device of the CLARK type" covers a well-known concept within the measuring electrode technology. This electrode device was first described by Clark at an annual meeting held by the American Society for Artificial Internal Organs in 1956, and it is distinguishable from the electrochemical measuring electrode devices for polarographically measuring thepartial pressure of oxygen known up until then in that the electrode device of the CLARK type comprises an oxygenpermeable membrane separating an anode and a cathode of the electrode device from the measuring medium, and in that an electrolyte solution is arranged in an electrolyte chamber defined by the membrane and communicates electrolytically and chemically with the anode and the cathode.

In accordance with the principles of the electrode device of the CLARK type, the partial pressure of oxygen of the electrolyte solution constitutes a measure of the partial pressure of oxygen of the medium as oxygen diffuses from the medium into the electrolyte solution. Provided that the supply of oxygen from the medium is sufficiently high and further provided that the rate of diffusion of oxygen through the membrane is sufficiently high, the partial pressure of oxygen of the electrolyte solution is a true measure of the partial pressure of oxygen of the medium.

Normally, the cathode is made of a metal which is capable of catalysing cathodic reduction of oxygen, and the anode is made of an oxidizable metal. Suitable cathode metals are noble metals such as platinum and gold and a suitable anode metal is silver. Conventionally, the electrolyte solution is a pH-stabilized chloride ion-containing aqueous solution, but the solvent may also be an organic solvent such as glycol. The membrane is of a foil-shaped plastic material with appropriate oxygen diffusion properties and is normally made of e.g. polyethylene, polypropylene, polytetrafluoroethylene or suitable combinations thereof. Between the cathode and the anode, the potential difference of approximately $-0.6$ V is maintained in order to permit the reduction of oxygen at the cathode. As a result of the reduction of oxygen at the cathode, a current is generated, and the current which is called the electrode response comsequently constitutes a measure of the concentration or partial pressure of oxygen of the electrolyte solution and in the electrode device of the CLARK type further a measure of the partial pressure of oxygen of the medium separated from the electrolyte solution by the membrane.

As the direct contact between the oxygen-reducing cathode surface and the sample is avoided due to the membrane, the oxygen electrode device of the CLARK type is especially applicable for measuring the partial pressure of oxygen of physiological media or liquids. Thus errors of measurement caused by the presence of other substances such as proteins, which otherwise might give rise to the so-called "poisoning" of the cathode, are avoided.

However, when using an electrode device of the CLARK type, other measuring technical problems occur. After using the electrode for some time, the electrode response, when shifting between samples with different oxygen levels, will become slow (the time constant of the electrode device becomes high). As a result of the slow response, the electrode device will exhibit hysteresis at some applications such as in automatic oxygen analysers in which the electrode response after a relatively short time of the order of 1–2 minutes is used for calculating the oxygen level of an unknown sample. Due to the hysteresis, the measuring result of a given sample will depend on the oxygen content of the previous samples.

The slow response is therefore particularly disadvantageous when the electrode device is applied in automatic analysing equipment in which a very high analysing frequency or rate is aimed at.

In a notice in Proceedings of the Physiological Society, December 1969, 29P-30P, a polarographic oxygen electrode device of the CLARK type is described in which, inter alia, the presence of catalase was observed to apparently reduce some form of oxygen storage in the electrode. This indicated that $H_2O_2$ accumulation in the electrolyte solution was chiefly responsible.

It may be hypothesized that an accumulation of $H_2O_2$ in the electrolyte solution plays a role in the operation of a Clark-type electrode device, and that said accumulation may be explained by the fact that the cathodic reduction of $O_2$ to $H_2O$ occurs in a two-step reaction in which $H_2O_2$ constitutes an intermediate. The second step of the reaction, in which the intermediate $H_2O_2$ is decomposed to $H_2O$, is delayed in an aged oxygen electrode device. The two reaction steps are:

$$O_2 + 2H^+ + 2e^- \rightarrow H_2O_2 \quad (1)$$

$$H_2O_2 + 2H^+ + 2e^- \rightarrow 2H_2O \quad (2)$$

The overall reaction is:

$$O_2 + 4H^+ + 4e^- \rightarrow 2H_2O \quad (3)$$

Since the rate constant of the $O_2$ decomposition according to step (1) is large, the rate of step (1) is high. The rate of step (2) is determined by the rate constant of the $H_2O_2$ decomposition, and this rate constant appears to be much lower in an ages electrode device than in a non-aged electrode device. For the aged electrode device, step (2) will determine the rate of the overall reaction.

In a non-aged electrode device, in which step (2) is not delayed, the conditions of diffusion of oxygen from the sample to the cathode determine the rate of the overall reaction. Due to the large rate constant of step (2), no accumulation of $H_2O_2$ is observed in such a non-aged electrode device.

The slow response of step (2) in an aged electrode device has the effect that in such an aged electrode device, which is in a steady-state condition at a constant oxygen level, the part of the electrolyte solution adjacent to the cathode will contain a specific amount of $H_2O_2$ (the equilibrium concentration of $H_2O_2$). The equilibrium concentration of $H_2O_2$ stabilizes on a level so that the rate of formation of $H_2O_2$ according to step (1) and the sum of the rate of decomposition of $H_2O_2$ according to step (2) and the rate at which $H_2O_2$ diffuses away from the electrolyte solution part adjacent to the cathode and to the adjoining electrolyte solution are equivalent.

As can be seen, the response of the oxygen electrode device will be a current consisting of two components: One component which is attributable to the oxygen reduction according to step (1), and one component which is attributable to the $H_2O_2$ reduction according to step (2).

Consequently, it is evident that in a case in which the surrounding oxygen level changes or varies, e.g. by bringing a sample of a different oxygen level into contact with the electrode device, the electrode device will not give a stable response (equilibrium current) until a new $H_2O_2$ equilibrium concentration in the electrolyte solution has been reached.

Furthermore, it is clear that the calculation of the concentration of oxygen on the basis of measuring results provided by means of an electrode device, when the electrode device is not in a state of equilibrium, i.e. when the electrode response or electrode current is different from the equilibrium current, will provide results which are different from the results provided by means of an electrode device which is in its equilibrium state.

By modifying the electrode device so that the $H_2O_2$ concentration is kept at or approximately at zero, $H_2O_2$ being spontaneously decomposed to $H_2O + \frac{1}{2}O_2$, the partial reaction will be:

$$O_2 + 2H^+ + 2e^- \rightarrow H_2O_2 \quad (4)$$

$$H_2O_2 \rightarrow H_2O + \frac{1}{2}O_2 \quad (5)$$

The overall reaction is as shown above:
$$O_2 + 4H^+ + 4e^- \rightarrow 2H_2O \quad (6)$$

As step (5) proceeds rapidly, $H_2O_2$ will not accumulate in the electrolyte solution and the diffusion conditions of oxygen from the sample to the cathode will determine the rate of the overall reaction. Consequently, such a modified electrode device will generate a stable electrode response soon after a change of the oxygen partial pressure.

The above-mentioned reduction of the $H_2O_2$ level in the electrolyte solution by the addition of catalase is not suitable for improving an electrode device for polarographically measuring the partial pressure of oxygen in routine clinical analyses, e.g. in the so-called blood gas analysers installed in hospitals in connection with operating sections or in central laboratories.

To have a blood gas analyser accepted by the users, it is of the greatest importance that maintenance work is moderate and substantially based on ready-to-use products, which on the one hand reduces the time spent on maintenance work and on the other hand reduces the risk of incorrect analyses caused by errors made by an operator in connection with maintenance work.

For routine maintenance of an electrode device of the CLARK type in a blood gas analyser, the membrane and the electrolyte solution are to be replaced approximately once a month. However, an electrolyte solution containing catalase cannot be prepared as a ready-to-use product, as the decline in the activity of the catalase during the normal storage periods would be excessive. Furthermore, to add catalase to the fresh electrolyte solution at the site of use immediately before the replacement of the electrolyte solution is to be considered a measure which cannot be accepted, because hospital personnel themselves are not willing to carry out preparation work such as preparing reagents, electrolyte solutions or other liquid mixtures.

Therefore, the object of the present invention is to provide an electrochemical measuring electrode device for polarographically measuring the partial pressure of oxygen, particularly an electrochemical measuring electrode device of the CLARK type or a component for a CLARK type electrode device, i.e. an electrode device of the CLARK type exclusive of the electrolyte solution and the membrane to be placed or arranged on said component at the site of use, which electrode device of the CLARK type or which component for an electrode device of the CLARK type is capable of generating reproducible and fast responses which are substantially independent of the age and the previous life of the electrode device and which electrode device of the CLARK type or which component for an electrode device of the CLARK type is at the same time as easy to maintain as the known electrode devices of the CLARK type.

This object is fulfilled by an electrochemical measuring electrode device of the abovedefined type, i.e. for polarographically measuring the partial pressure of oxygen in an electrolytic medium and comprising:

a cathode, said cathode being capable of reducing oxygen and defining an exposed oxygen-reducing cathode surface, an anode, said anode defining an exposed anode surface, said exposed oxygenreducing cathode surface and said exposed anode surface being arranged relative to one another so as to communicate electrolytically with one another through said electrolytic medium, and a non-biological catalytic means arranged so as to communicate catalytically with $H_2O_2$ generated at said exposed oxygen-reducing cathode surface and effective for promoting the decomposition of said $H_2O_2$, said catalytic means being substantially inert to the other electrode response-determining components to which it is exposed in operation of the electrode device and being substantially stable under the chemical and electrochemical conditions to which it is exposed in the electrode device.

The above-defined electrochemical measuring electrode device according to the invention is preferably an electrode device of the CLARK type of constitutes a component for an electrode device of the CLARK type as explained above. When the electrochemical measuring electrode device according to the invention is an electrode device of the CLARK type, the electrode device according to the invention further comprises a membrane, said membrane being permeable to oxygen and covering at least said exposed oxygen-reducing cathode surface and said exposed anode surface and further defining an electrolyte chamber in front of said surfaces, and an electrolyte solution, said electrolyte solution being confined in said electrolyte chamber and constituting said electrolytic medium through which said exposed anode surface and said catalytic means communicates with said exposed oxygen-reducing cathode surface.

In the present specification and claims, the term "stable", as used in describing the catalytic means, is intended to indicate that the catyalytic means will substantially retain its efficiency for promoting the decomposition of $H_2O_2$ under the conditions to which it is exposed in the electrode device; e.g. when the catalytic means is incorporated in the membrane or in a supporting structure, as explained below, the catalytic means should substantially retain its efficiency for promoting the decomposition of $H_2O_2$ during the normal period between replacements of the electrolyte solution and the membrane.

The term "non-biological" indicates that the catalytic means does not comprise a catalytic principle which involves an enzyme or another protein or other biologically generated structure comprising peptide or other organic bonds which would confer instability thereto.

The catalytic means is preferably a solid catalytic means which is substantially insoluble in the electrolyte even under the conditions prevailing during operation of the electrode and is preferably provided at a position close to the oxygen-reducing cathode surface of the electrode device.

As will appear from the figures and the appertaining description, the good response conditions aimed at are obtained with the electrode device according to the invention. Futhermore, it is extremely easy to prepare preprocessed electrode devices according to the invention or preprocessed components for use in the electrode devices according to the invention and no durability problems have been ascertained in connection with the preprocessed electrode devices or components.

It should be noted that certain inorganic catalysts otherwise known to be effective for promoting the decomposition of $H_2O_2$, have been found not to show the essential stability under the chemical and electrochemical conditions to which the catalyst is exposed in the electrode device. Thus, colloidal silver and manganese dioxide have been found to be dissolved in the electrolyte of CLARK electrodes and thereby apparently to be converted into components which do not act as catalysts for the decomposition of $H_2O_2$. Activated carbon has been found to absorb oxygen and thereby to interfere with the current generation in the electrode.

Although the electrochemical measuring electrode device according to the invention is preferably of the CLARK type of constitutes a component for an electrode device of the CLARK type, i.e. is adapted to be provided with a membrane and an electrolyte solution as described above, it is believed that the teaching of the present invention, i.e. the provision of a stable, non-biological catalytic means for promoting the decomposition of $H_2O_2$ generated in the electrolytic medium as an oxygen-reduction intermediate is also applicable in connection with electrochemical measuring electrode devices for polarographically measuring the partial pressure of oxygen which electrode devices are not of the CLARK type, i.e. which electrode devices do not comprise a membrane and are not adapted to be provided with a membrane, but where accumulation of $H_2O_2$ generated as an oxygen reduction intermediate would likewise interfere with the measurement.

The catalytic means may be a means comprising a noble metal, that is, a metal which is placed below, or has a higher oxidation potential than, silver in the electrochemical series, and/or a metal of the platinum group. In the present context, the term "comprising" is to be interpreted in the broad sense.

In the preferred embodiment of the electrode device according to the invention, the catalytic means is constituted by a platinum black means. The platinum black means may be constituted by platinum black particles, and the platinum black particles may be received by the membrane, or alternatively, the electrode device further, preferably, comprises a support structure, the support structure being permeable to $H_2O_2$ and water, and the platinum black particles being received by the support structure. The support structure means may constitute a covering of at least part of the membrane. It is preferred that the cross-sectional area of the individual platinum black particles is substantially smaller than the exposed oxygen-reducing cathode surface area. In particular, it is preferred that the particulate platinum black is substantially constituted by particles, the maximum diameter of which is less than 1 $\mu$m.

The platinum black particles received by the support structure or received by the membrane may preferably be located at the side of the membrane facing the electrolyte chamber. Although the catalytic means constituted by the platinum black particles is preferably received by a support structure preferably constituting a covering of at least part of the membrane, the catalytic means constituted by the platinum black particles may, alternatively, be constituted by a separate catalytic means componet which is received in the electrode device according to the invention as defined above, however e.g. protrudng into the electrolyte chamber or located adjacent to or in front of the oxygen-reducing cathode surface. By providing the catalytic means of the electrode device as platinum black particles received by the membrane or received by the support structure preferably constituting a covering of at least part of the membrane, it is ensured that the effective promotion of decomposition of $H_2O_2$ takes place at the appropriate place in relation to, i.e. adjacent to or in front of the exposed oxygenreducing cathode surface.

To ensure effective $H_2O_2$ reduction in the entire section of the electrolyte chamber communicating with the cathode surface, the platinum black particles are preferably in accordance with the present invention provided in such an amount and arranged relative to the exposed oxygen-reducing cathode surface in such a manner that the concentration of $H_2O_2$ is maintained substantially at zero in any volume of the electrolyte in the electrolyte chamber electrolytically communicating with the oxygen-reducing cathode surface, e.g. in a part of the electrolyte chamber having the oxygen-reducing cathode surface as a center and being within a distance from the cathode surface of max. 100 times the cathode surface diameter.

In connection with an oxygen electrode device according to the invention comprising a 20 $\mu$m diameter platinum cathode and a 20 $\mu$m polypropylene membrane, arranged at a distance of approx. 0–5 $\mu$m from the exposed oxygen-reducing cathode surface, it is preferred that the platinum black particles received by said support structure constituting a covering of at least part of the membrane are present in a surface density of 1-6000 µg/cm², preferably 20-600 µg/cm².

The platinum black particles may be arranged in direct contact with the electrolyte solution. Alternatively, the platinum black particles may be incorporated in a material which is permeable to $H_2O_2$ and water to avoid the electron-conducting contact between the platinum black particles and the cathode. Suitable materials are polyurethane, cellulose acetate, polyvinyl acetate and cellophane.

The electrode device according to the present invention may, e.g., be an electrode device of CLARK type constituting a component of, e.g., a blood gas analyser for analysing samples of whole blood, or it may, e.g., be a transcutaneous electrode device. The transcutaneous electrode device will preferably further comprise means for thermostatically heating the electrode device to a predetermined temperature, said means comprising a temperature sensor means and a heating means.

The present invention also relates to a membrane for an electrochemical measuring electrode device for polarographically measuring the partial pressure of oxygen in a medium, said membrane being permeable to oxygen and being provided with a coating of at least part of the surface of said membrane, said coating comprising a non-biological catalytic means effective for promoting the descomposition of $H_2O_2$, said cayalytic means being substantially inert to the other electrode response-determining components to which it is exposed in operation of the electrode device when the membrane has been mounted on the electrode device and being substantially stable under the chemical and electrochemical conditions to which it is exposed in operation of the electrode device.

Preferred embodiments of the membrane according to the invention are discussed above in connection with the general description of the invention.

The present invention further relates to methods of preparing a membrane for an electrochemical measuring electrode device for polarographically measuring the partial pressure of oxygen, the membrane being of a plastic material permeable to oxygen. In accordance with a first method according to the present invention, the method comprises the following steps:
  providing a foil of said plastic material,
  providing a suspension of platinum black particles in an organic liquid,
  applying said suspension to a side surface of said foil of said plastic material,
  evaporating said organic liquid,
  heating said plastic material to a temperature in excess of its softening temperature, and
  forcing said platinum black particles into said plastic material foil being softened by applying mechanical pressure to said platinum black particles.

In accordance with another or alternative method according to the present invention, the method comprises the following steps:
  providing a foil of said plastic material,
  providing a suspension of platinum black particles in a plastic material in liquid state,
  said material being permeable to oxygen, $H_2O_2$ and water,
  applying said suspension to a side surface of said foil of said plastic material so as to provide a homogeneous liquid covering of said side surface of said foil, and
  solidifying said plastic material so as to establish a solidified covering of said side surface of said foil.

In the above-described first method according to the present invention, the organic liquid may e.g. be benzene or ethanol. In the alternative method, the plastic materials may, e.g., be dissolved in a solvent, and/or it may be in a monomeric or oligomeric state which is polymerized to form the solidified covering.

The platinum black particles constituting a stable, non-biological catalytic means effective for promoting the decomposition of $H_2O_2$ generated by the electrochemical measuring electrode device as an oxygen reduction intermediate may alternatively be applied to the membrane according to the invention by other techniques, such as printing techniques, rolling techniques or, quite generally, techniques involving gluing the platinum black particles to the plastic material of the membrane.

Figure 2:
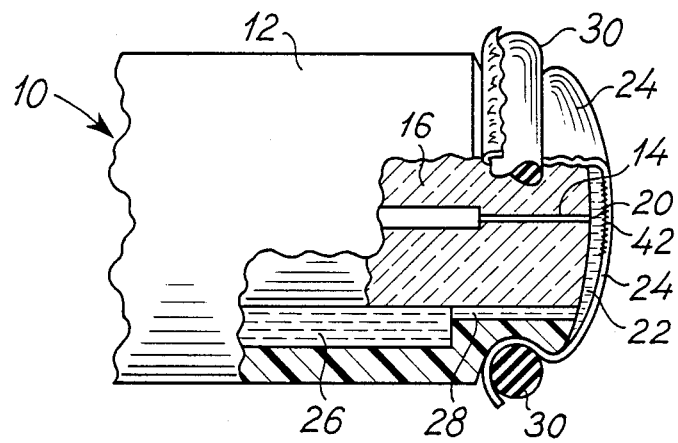
Figure 3:
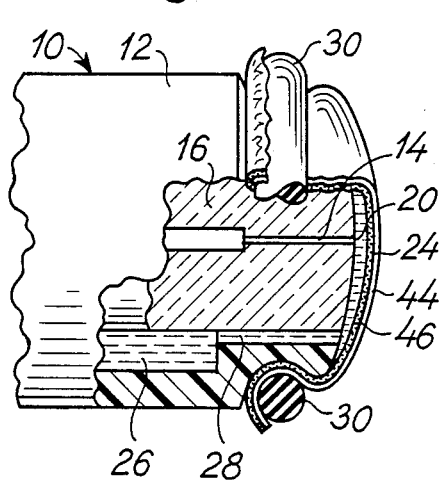
Figure 4:
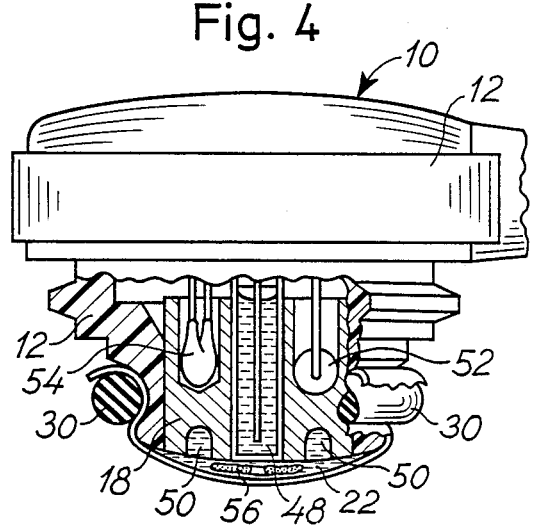
Figure 12:
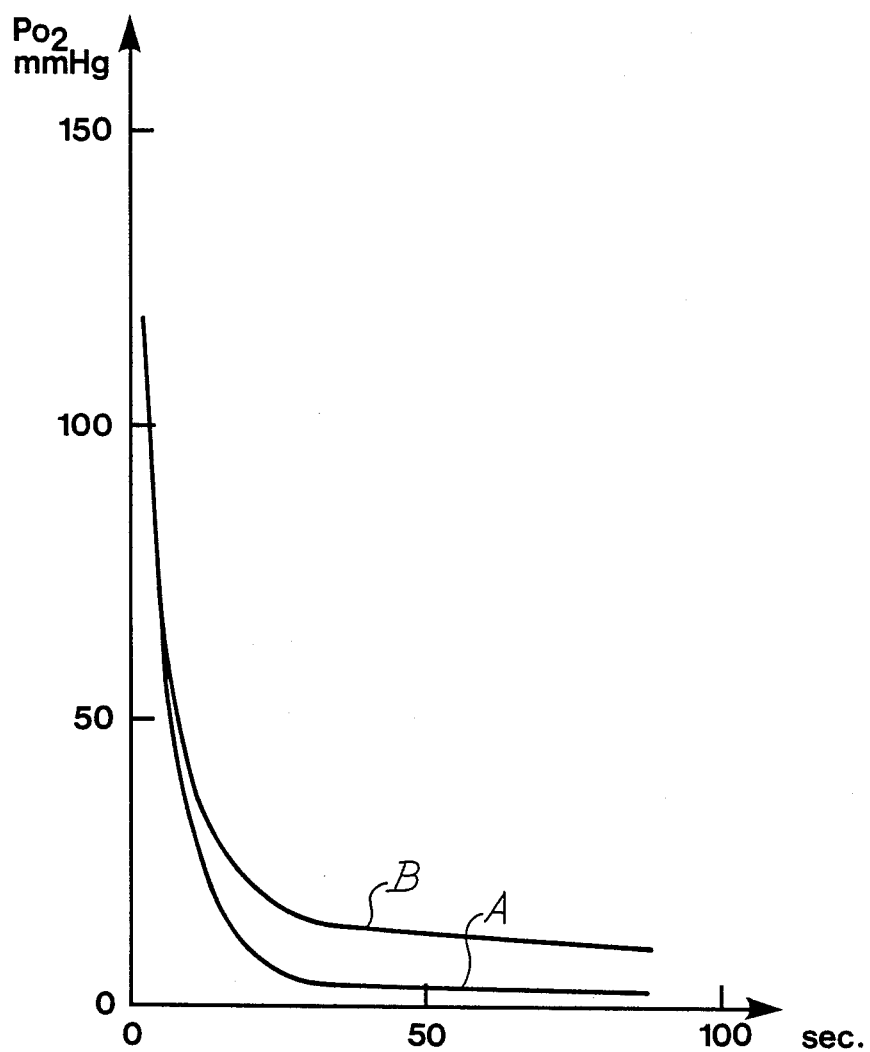
Figure 13:
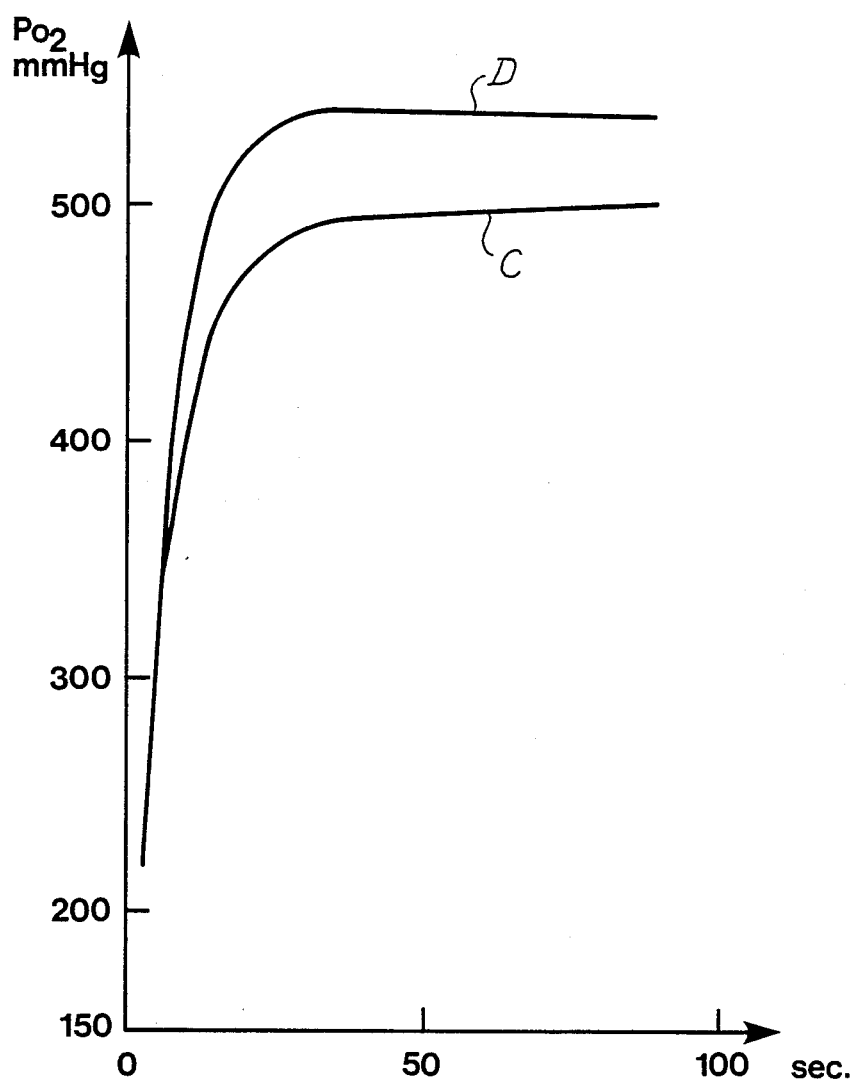

The invention will now be further described with reference to the drawings, in which FIG. 1 is a schematical view of a first, presently preferred embodiment of an electrochemical measuring electrode device of the CLARK type and according to the invention for measuring the partial pressure of oxygen, FIG. 2 is a perspective and partly broken away view of a front part of the electrochemical measuring electrode device shown in FIG. 1 also illustrating a first embodiment of a membrane according to the invention, FIG. 3 is a perspective and partly broken away view corresponding to the view of FIG. 2 also illustrating a second and presently preferred embodiment of the membrane according to the invention, FIG. 4 is a perspective and partly broken away view of a second embodiment of the electrochemical measuring electrode device according to the invention, the electrode device being a transcutaneous, polarographic and potentiometric electrode device, FIG. 5 is an elevational view of the first embodiment of the membrane accroding to the invention shown in FIG. 2, FIG. 6 is an elevational and partly broken away view of the second and presently preferred embodiment of the membrane according to the invention shown in FIG. 3, FIGS. 7, 8 and 9 are schematical views illustrating separate steps of a first method according to the invention of preparing the first embodiment of the membrane according to the invention, FIGS. 10 and 11 are schematical views of two alternative embodiments of the method according to the invention of preparing the second and presently preferred embodiment of the membrane according to the invention, FIG. 12 is a diagrammatical view illustrating the responses of an electrode device of the CLARK type according to the invention and the response of a conventional electrode device of the CLARK type, the electrode devices being identical to one another except for the catalytic means characteristic of the present invention, and FIG. 13 is a diagrammatical view illustrating the responses of the electrode devices mentioned above with reference to FIG. 12 in a different test set-up.

In FIG. 1, a first embodiment of an electrochemical measuring electrode device of the CLARK type according to the invention for measuring the partial pressure of oxygen in a blood sample is shown. The electrode device is designated by the reference numeral 10 in its entirety and comprises a plastic housing 12, a platinum cathode 14 which is constituted by a platinum wire of a diameter of 20 μm, which is sealed into a lead glass tube 16, and an anode 18. The platinum cathode 14 defines an active, exposed oxygen-reducing cathode surface 20, which is in contact with an electrolyte solution, which is confined in an electrolyte chamber 22 defined by an oxygen-permeable plastic membrane 24. As is evident from FIG. 1, the plastic housing 12 encircles the lead glass tube 16 so that an annular chamber 26 is defined between the plastic housing 12 and the lead glass tube 16. The annular chamber 26 communicates with the electrolyte chamber 22 through an electrolyte solution passage 28. The anode 18 is constituted by a silver/silver chloride coating of the lead glass tube 16 and communciates chemically with the electrolyte solution of the annular chamber 26 and further with the electrolyte solution of the electrolyte chamber 22 through the electrolyte solution passage 28.

On the membrane 24, platinum black particles of a particle size of less than 1 μm are applied, as shown in FIG. 2 or, alternatively as shown in FIG. 3. The membrane 24 is maintained in position in front of the end surface of the electrode device 10 by means of an O-ring 30 and covers the exposed oxygen-reducing surface 20 of the Pt-wire cathode 14. The electrolyte solution is an aqueous solution of the composition: 191 mmole $KH_2PO_4$, 298 mmole $Na_2HPO_4 2H_2O$, 139 mmole KCl, 0.26 mmole AgCl and thymol as a germicide. In use, a polarization voltage of −630 mV is supplied to the electrode device 10 from an external measuring apparatus 32 through a cable 34.

The electrode device is fitted in a measuring cell 36 of the type described in U.S. Pat. No. 4,160,714. In the measuring apparatus 32, the current generated by the electrode device by the reduction of oxygen is amplified and converted from analog to digital form in an A/D converter for calculating the partial pressure of oxygen, which is displayed on a first display 38 of the measuring apparatus 32. The measuring apparatus 32, further comprises a second display 40 for displaying the current generated by the electrode device 10 in digital representation.

In FIG. 2, the end part of the electrode device 10 according to the present invention is shown in greater detail also disclosing the structure of the membrane 24 which comprises a non-biological catalytic means constituted by platinum black particles effective for promoting the decomposition of $H_2O_2$ generated in the electrolyte solution by the reduction of oxygen. Although the catalytic means is preferably constituted by a covering of at least part of the membrane of the electrode device, the catalytic means may, alternatively, e.g., be a layer in an annular configuration or an annular groove arranged at the front end of the lead glass tube 16, e.g., encircling the cathode.

The membrane 24 is a circular piece of biaxially orientated polyproplyene foil of a thickness of 20 μm. The diameter of the membrane 24 is 13 mm and the central part of the membrane 24 contacting a sample is approximately 5 mm. In a central region 42 of the membrane 24, platinum black particles are pressed into the foil of the membrane. The central region 42 measures approximately 7 $mm^2$.

In FIG. 3, which is a partly broken away view of the end portion of the electrode device 10 basically corresponding to the view of FIG. 2, an alternative and presently preferred embodiment of the membrane 24 according to the invention is shown. The membrane 24 shown in FIG. 3 is a two-layer membrane, a first or outer layer of which is designated by the reference numeral 44 and constituted by the above-described biaxially oriented polypropylene foil. An inner layer 46 of the membrane 24 is constituted by a solidified plastic material including platinum black particles constituting a stable, non-biological catalytic means effective for promoting the decomposition of $H_2O_2$ generated in the reduction of oxygen.

The preparation of the first embodiment of the membrane 24 shown in FIG. 2 and the preparation of the second embodiment of the membrane 24 shown in FIG. 3 will be described in greater detail below with reference to FIGS. 7-9 and 10-11, respectively. In FIGS. 5 and 6, the first and the second embodiment, respectively, of the membrane 24 are shown in elevational views and in FIG. 6 in partly broken away view.

In FIG. 4, a second or alternative embodiment of the electrode device 10 according to the invention is shown. The electrode device shown in FIG. 4 is a transcutaneous and combined polarographic and potentiometric electrode device of the type described in the applicant's published international patent application PCT/DK81/00035, publication No. WO 81/02831 to which reference is made. In FIG. 4, components similar to the components described above with reference to FIGS. 1-3 are designated by reference numerals identical to the reference numerals of FIG. 1-3. In the transcutaneous, polarographic and potentiometric electrode device 10 shown in FIG. 4, the anode 18 is constituted by a solid silver body. Centrally within the solid silver body, a pH-electrode 48 is arranged. At the lower side surface of the silver body 18, recesses 50 are provided which are filled by the electrolyte solution and constitute electrolyte reservoirs. In two further recesses of the silver body 18, a Zener diode 52 and an NTC resistor 54 are arranged. The Zener diode 52 and the NTC resistor constitute a heating element and a temperature detector element, respectively, of the transcutaneous polarographic and potentiometric electrode device, as is well-known in the art. In front of the pH-electrode 48 and further in front of the cathode of the electrode device, not shown in FIG. 4, a spacer structure 56 is arranged. The spacer structure is constituted by a water and $H_2O_2$ and carbon dioxide permeable plastic element further comprising platinum black particles constituting a catalytic means effective for promoting the decomposition of $H_2O_2$ formed by the reduction of $O_2$. As is evident from FIG. 4, the spacer structure 56 is of a basically annular configuration.

The platinum black particles of the membrane 24 or of the spacer structure 56 are prepared by grinding commercially available platinum black of the type FLUKA No. 81110. The commercially available platinum black has a variable grain size of approx. 5 μm.

When preparing the ground platinum black particles, 1 g is weighed out and suspended in benzene at a concentration of approx. 20 mg/ml. The suspension is transferred to a beaker filled with small glass beads, and stirred on a magnetic stirrer of a conventional laboratory type for 24 hours. Thus a particularly finely distributed platinum black (dust) is obtained with a comparatively uniform particle size distibution and with an average particle diameter <0.5 μm.

The platinum black dust is easily suspended in the suspending agent.

In accordance with a first method of preparing a membrane according to the invention, 10 μl of a benzene or ethanol suspension of the above-described platinum particles is, as shown in FIG. 7, taken out by means of a Carlsberg pipette 58 and transferred to a circular polypropylene foil 60. As is evident from FIG. 7, the foil 60 may be supported on a support structure 64 which further includes a heating element 66. In FIG. 7, the 10 μl suspension including the platinum black particles is designated the reference numeral 62. The suspending agent is evaporated by standing for about 5 minutes. Alternatively, the evaporation could be performed by applying heat to the support structure 64 from the heating element 66. Thereafter, as is evident from FIG. 8, a TEFLON ® foil 68, the melting point of which exceeds 175° C., is arranged on top of the foil 60 with the layer of platinum black particles 62 from which the dispersing agent has been evaporated. A pressing tool 70 which also includes a heating element 72 is brought into contact with the upper side surface of the TEFLON ® foil 68 as indicated by an arrow 73 and pressed against the foil 60 with a pressure of approximately 300 kg/cm$^2$ (29.4×10$^6$ N/m$^2$), while heat is applied to the pressing assembly from the heating elements 66 and 72 in order to heat the foils 60 and 68 to a temperature of approximately 130° C. The above pressure is maintained for a period of time of approximately 10 min., whereupon the platinum black particles have been pressed into the foil material 60.

After the above 10 min. period of time, the heating elements 66 and 72 are disconnected from their supply. When the system has cooled to room temperature, the pressing tool is elevated and, as is evident from FIG. 9, the TEFLON ® foil 68 is removed. The platinum black particles adhere completely to the polypropylene foil 60.

From an electrode response time point of view, the above-described first method of preparing a membrane according to the invention may be the most advantageous as the membrane prepared in accordance with the above-described method basically has characteristics as to strength and permeability to oxygen which are identical to the characteristics of a polypropylene membrane which does not include platinum black particles. However, it has been found that this method may sometimes result in a membrane which may give rise to a quiescent or zero current of the electrode device when the membrane is arranged on the electrode device and maintained in poisiton by means of its O-ring as shown in FIGS. 1-3. This is believed to be due to the fact that some of the platinum black particles which should have been pressed into the membrane material protrude from the inner side surface of the membrane and are consequently brought into contact with the exposed cathode surface so that a galvanic current is generated by the contact between the exposed cathode surface and the platinum black particles. Thus, in this method, it seems important to ensure that substantially all of the platinum black particles are pressed into the membrane material.

In accordance with a second and presently preferred embodiment of preparing the membrane according to the invention, the platinum black particles are suspended in a plastic material which is in a liquid state, e.g., in solution, whereupon the suspension is applied to the polypropylene foil and solidified, e.g., by evaporation. Two alternatives of applying the suspension to the foil in accordance with the above-described presently preferred embodiment of the method according to the invention are shown in FIGS. 10 and 11.

In FIG. 10, the suspension of the platinum black particles in the liquid plastic material is poured onto an outer or upper side surface of the polypropylene foil 60 which is arranged in an oblique position, whereupon the suspension which is designated by the reference numeral 74 in FIG. 10 flows down the oblique foil whereby a homogenous suspension layer is provided and is solidified, e.g., by evaporation.

The suspension 74 may, as is shown in FIG. 11 alternatively be applied to the outer or upper side surface of the foil 60 in a screening process by employing a squeegee or spatula 76.

The liquid plastic material may, e.g., be prepared as a solution of 0.35 g PUR (polyurethane) in 5 ml DMF (dimethylformamide), and 20 ml THF (tetrahydrofuran) which may be prepared within a few hours. In 3 ml of this solution, 5 mg platinum black particles are suspended and ground by stirring with a magnetic stirrer for about two hours in a beaker of diameter 20 mm filled with about 20 glass beads of a diameter of 3 mm.

As will be understood, the response time of the electrode device comprising the above described second and presently preferred embodiment of the membrane accordint to the invention may be slightly slower than the response time of the electrode device comprising the above-described first embodiment of the membrane according to the invention if the membrane thickness is not reduced to compensate for the added layer. However, the increase in the response time by applying the inner layer 46 to the outer layer 44 of the membrane 24 shown in FIG. 3 only amounts to approximately 50%, and the response time of the electrode device shown in FIG. 3 may obviously be reduced by simply decreasing the thickness of the outer membrane layer 44. The membrane 24 shown in FIGS. 3 and 6 has the advantage that the platinum black particles are all embedded in the layer 46 and thus cannot give rise to a quiescent current or zero current.

In FIG. 12, a diagram is shown illustrating the response A of an aged oxygen electrode device as shown in FIGS. 1 and 2 according to the invention comprising a membrane of the type described above with reference to FIGS. 2 and 5 and prepared as described above with reference to FIGS. 7-9 and the response B of the same electrode device comprising a polypropylene membrane of a conventional type, i.e. not including platinum black particles.

The responses were recorded in an experiment in which the electrode devices were mounted in a set-up of the type shown in FIG. 1 for measuring the oxygen partial pressure on gas samples. Atmospheric air saturated with aqueous vapour, i.e. air of an oxygen partial pressure of 145 mm Hg (19.3 kkPa) was introduced into the measuring cell 36 every 6 minutes and conducted past the electrode device.

After the oxygen electrode device has been mounted in the measuring cell for approx. 3 days, a sample of the composition of 95% argon, 5% $CO_2$, i.e. of an oxygen partial pressure of zero, was introduced into the measuring cell. The digitized response of the electrode device was recorded every 2 seconds and converted to mm Hg on the basis of calibration data at 145 mm Hg. The two response curves A and B shown in FIG. 3 were plotted on the basis of the response data thus recorded.

It is seen that after 90 seconds the electrode current and/or the response B of the conventional electrode device reaches a value corresponding to an oxygen partial pressure of approximately 9 mm Hg, whereas the electrode current of the response A of the electrode device according to the invention already after 45 seconds reaches a stable value corresponding to an oxygen partial pressure of 2 mm Hg. Thus it can be seen that the response of the electrode device of the present invention reaches its stable level considerably faster than the conventional electrode device.

Based on the theoretical reflections above, it is evident that the response curve B of the conventional ages electrode device will be positioned above the response curve A of the electrode device according to the invention, when the oxygen level in the sample is lower than the oxygen level at which the electrode device has stabilized. This is due to the fact that the $H_2O_2$ level in the electrolyte solution while the response curve is recorded is higher than the level of $H_2O_2$ originating from the present oxygen level and thus provides a higher current than the current to be expected from the present oxygen level.

The rate of the response is usually expressed by the time constant of the electrode device, which is approximately 5 seconds for a non-aged conventional oxygen electrode device. The same value is ascertained for the electrode devices according to the invention. Aged conventional oxygen electrode devices have a small time constant during the first part of the response and a large time constant during the last part of the response.

In connection with measurements on samples with an oxygen level lower than the oxygen lever at which the electrode device has stabilized (145 mm Hg), the time constant during the last part of the response for aged conventional oxygen electrode devices was experimentally found to be more than 15 seconds.

On the basis of the response curves, it is estimated that the analysing time may be reduced by more than 50% in an analysing apparatus in which the electrode device according to the invention replaces the conventional device.

In FIG. 13, the response D of an aged electrode device according to the invention and of the type described above with reference to FIG. 12 and the response C of the conventional eletrode device also described above with reference to FIG. 12 are shown.

With the one exception that a sample of a high oxygen level (80% $O_2$, 5% $CO_2$, 15% $N_2$) was used instead of a sample of an oxygen level of zero, the experimental work which led to the plotting of FIG. 13 was carried out in the same manner as described in connection with FIG. 12.

In this case a lower oxygen content was recorded (as expected) when employing the conventional electrode device than when employing the electrode device according to the invention.

We claim:

1. A polarographic electrode device of the Clark type for polarographically measuring the partial pressure of oxygen, comprising:
    (a) a cathode capable of reducing oxygen and defining an exposed oxygen-reducing cathode surface;
    (b) an anode defining an exposed anode surface;
    (c) an $O_2$-permeable membrane;
    (d) an electrolyte chamber defined at least in part by said $O_2$-permeable membrane, and containing therein said exposed oxygen-reducing cathode surface and said exposed anode surface;
    (e) an electrolyte solution confined in said electrolyte chamber and providing an electrolyte medium through which said anode surface and cathode surface communicate with one another; and
    (f) non-silver noble metal particles contained in said electrolyte chamber arranged so as to be in communication with the electrolyte solution and adjacent to the exposed oxygen-reducing cathode surface.

2. An electrode device according to claim 1, in which the particles comprise a platinum group metal.

3. An electrode device according to claim 2, in which the particles comprises platinum black particles.

4. An electrode device according to claim 3, in which said platinum black particles are received by said membrane.

5. An electrode device according to claim 4, in which the platinum black particles are present in a surface density of 1–6000 $\mu g/cm^2$.

6. An electrode device according to claim 3, in which the cross-sectional area of the individual platinum black particles is smaller than the exposed oxygen-reducing cathode surface area.

7. An electrode device according to claim 6, in which the platinum black particles are substantially constituted by particles having a maximum diameter of less than 1 $\mu m$.

8. An electrode device according to claim 3, which further comprises a support structure, said support structure being permeable to $H_2O_2$ and water, and said platinum black particles being received by said support structure.

9. An electrode device according to claim 1, further comprising means for thermostatically heating the electrode device to a predetermined temperature and comprising a temperature sensor means and a heating means.

* * * * *